US006887907B2

(12) United States Patent
Guillard et al.

(10) Patent No.: US 6,887,907 B2
(45) Date of Patent: May 3, 2005

(54) PROCESS AND APPARATUS FOR THE PRODUCTION OF DIMETHYL ETHER

(75) Inventors: Alain Guillard, Paris (FR); Emmanuel Schmidt, Vincennes (FR)

(73) Assignee: L'Air Liquide - Societe Anonyme a Directoire et Conseil de Surveillance pour l'Etude et l'Exploitation des Procedes Georges Claude, Paris Cedex (FR)

( * ) Notice: Subject to any disclaimer, the term of this patent is extended or adjusted under 35 U.S.C. 154(b) by 0 days.

(21) Appl. No.: 10/773,163

(22) Filed: Feb. 9, 2004

(65) Prior Publication Data

US 2004/0176481 A1 Sep. 9, 2004

Related U.S. Application Data

(60) Provisional application No. 60/451,629, filed on Mar. 5, 2003.

(51) Int. Cl.$^7$ .............................................. C07C 27/00
(52) U.S. Cl. ........................ 518/700; 518/702; 518/703; 518/705
(58) Field of Search ................................. 518/700, 702, 518/703, 705

(56) References Cited

U.S. PATENT DOCUMENTS

| 3,920,717 A | | 11/1975 | Marion |
| 5,177,114 A | * | 1/1993 | Van Dijk et al. ........... 518/703 |
| 5,392,594 A | | 2/1995 | Moore et al. |
| 6,117,916 A | | 9/2000 | Allam et al. |
| 2003/0092780 A1 | | 5/2003 | Sogge et al. |

* cited by examiner

Primary Examiner—J. Parsa
(74) Attorney, Agent, or Firm—Young & Thompson

(57) ABSTRACT

In a process for the use of a hydrocarbon feedstock (10) by reacting the feedstock in a reactor (11) with oxygen (9) to form a synthesis gas containing at least carbon monoxide, carbon dioxide and hydrogen and subjecting the synthesis gas to a conversion process comprising an exothermic reaction to produce dimethyl ether in a converter (15), the converter operating at an operating pressure, said oxygen being provided to the reactor at an oxygen pressure, the synthesis gas is produced at a pressure higher than the operating pressure of the converter.

15 Claims, 1 Drawing Sheet

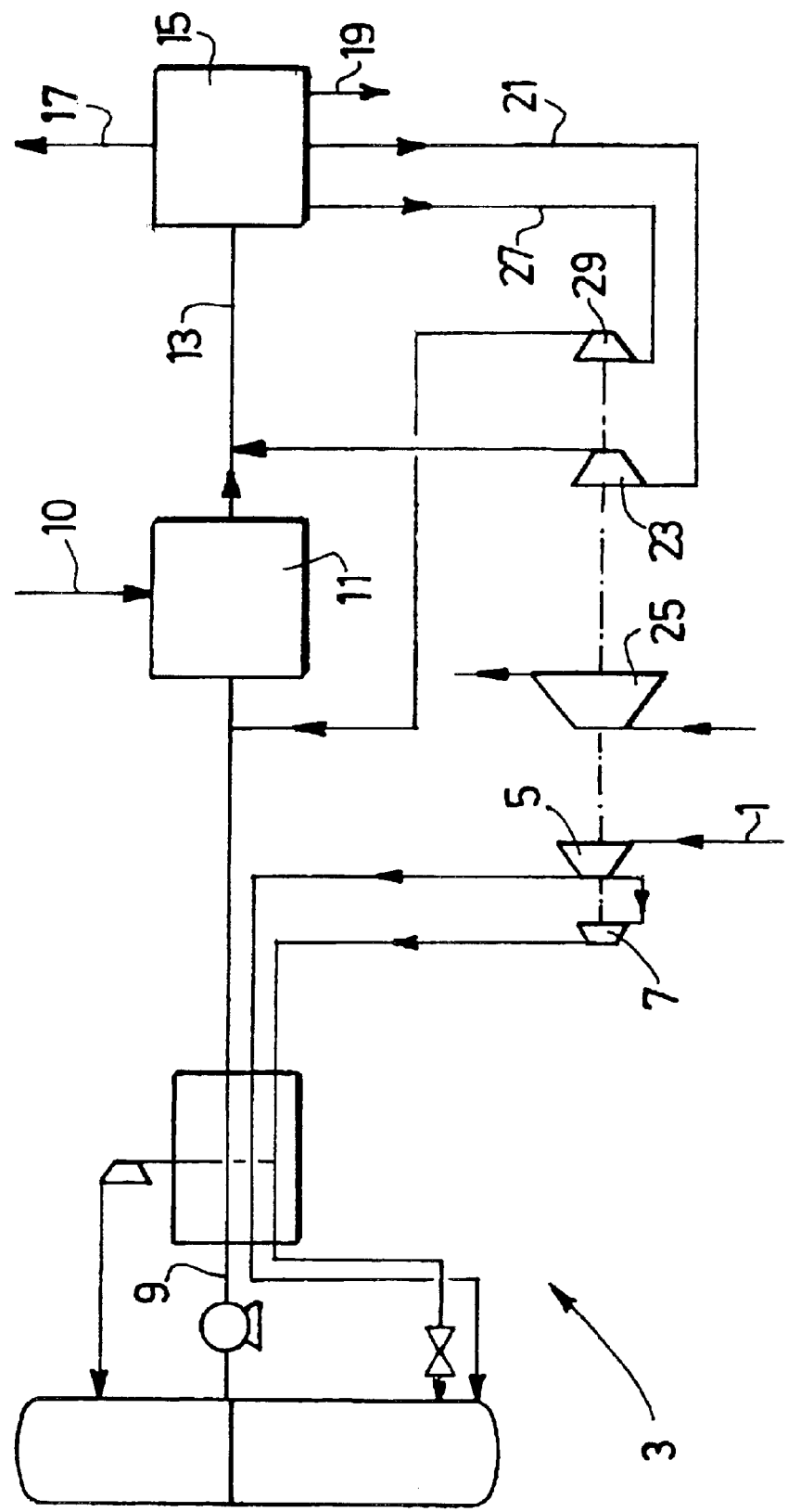

PROCESS AND APPARATUS FOR THE PRODUCTION OF DIMETHYL ETHER

TECHNICAL FIELD OF THE INVENTION

The present invention relates to a process and apparatus for the production of dimethyl ether (DME).

All the pressures mentioned are absolute pressures.

BACKGROUND OF THE INVENTION

Methanol is produced by contacting a synthesis gas containing at (east carbon monoxide, carbon dioxide and hydrogen with a catalyst. This synthesis gas is converted to methanol in a separate vessel.

DME can be produced either by direct processes or indirect (two step) processes.

The direct processes convert synthesis gas to methanol and then methanol to DME in the same converter.

The two step processes include the conventional two step process in which methanol is dehydrated in a catalytic fixed bed vessel and the vessel effluents are cooled and distilled to produce DME and methanol which is recycled to the converter.

The Lurgi Mega DME process uses natural gas to produce methanol which is then treated in a vessel to produce a mixture of DME, water and other hydrocarbons. The mixture is then distilled.

The Haldor Topsoe DME process converts synthesis gas to methanol and then converts the methanol to DME in a fixed bed vessel.

Most of these processes use an air separation unit (ASU) to produce oxygen at high pressure to convert natural gas to synthesis gas, the synthesis gas either being sent to a single converter where it is converted to methanol and then to DME in a direct process or being sent to a first converter to be converted to methanol, the methanol then being removed and converted to DME in a two step process.

As described in U.S. Pat. No. 6117916, an ASU produces oxygen at 40 bar and the oxygen reacts with steam and natural gas in a partial oxidation reactor to produce synthesis gas. The synthesis gas at 40 bar is then compressed to 70 bar and is sent to a methanol reactor, thereby producing methanol at 66 bar.

Usually two synthesis gas compressors in parallel are used to avoid maintenance problems. These compressors are costly both in capital investment and in terms of upkeep.

SUMMARY OF THE INVENTION

According to an object of this invention, in a process for the use of a hydrocarbon feedstock by reacting the feedstock in a reactor with oxygen to form a synthesis gas containing at least carbon monoxide, carbon dioxide and hydrogen and subjecting the synthesis gas to a conversion process comprising an exothermic reaction to produce dimethyl ether in a converter, the converter operating at an operating pressure , said oxygen being provided to the reactor at an oxygen pressure following separation of cooled compressed air compressed in an least one air compressor, the improvement consisting in that the synthesis gas is produced at a pressure such that the synthesis gas is sent from the reactor to the converter without undergoing a compression step, and the air separation unit supplies oxygen to the reactor at an oxygen pressure greater than the operating pressure of the reactor.

The synthesis gas is produced at a pressure higher than the operating pressure of the converter at least 1 bar higher, possibly at least 3 bar higher, or even at least 5 bar higher, than the operating pressure of the converter.

The hydrocarbon feedstock may be natural gas.

At least one of methanol, carbon dioxide and unreacted synthesis gas may also be present at the outlet of the converter.

Dimethyl ether, produced by the exothermic reaction, may be produced by a direct process or by an indirect process, by converting synthesis gas to methanol and then converting the methanol to dimethyl ether.

For example, the converter may produce a mixture of methanol and dimethyl ether, the mixture is separated to produce substantially pure dimethyl ether and substantially pure methanol and the substantially pure methanol is recycled to an inlet of the converter. Some carbon dioxide may be present at the converter outlet; in this case carbon dioxide is recycled to an inlet of the reactor following compression in a carbon dioxide compressor. In addition some unreacted synthesis gas is present at the converter outlet and this may be recycled to the converter inlet following compression in a recycle synthesis gas compressor.

A steam turbine may be coupled to at least one of the recycle synthesis gas compressor, the carbon dioxide compressor, an air booster and an air compressor.

The reactor may be a partial oxidation reactor or an autothermal reactor.

The air separation unit produces oxygen at an oxygen pressure greater than the operating pressure of the reactor, preferably at least 5 bar greater than the operating pressure of the reactor, more possibly at least 3 bar greater than the operating pressure of the reactor, possibly at least 1 bar greater than the operating pressure of the reactor.

According to a further aspect of the invention, in an apparatus for the use of a hydrocarbon feedstock by reacting the feedstock in a reactor with oxygen to form a synthesis gas containing at least carbon monoxide, carbon dioxide and hydrogen; a reactor, means for sending the feedstock and oxygen to the reactor, means for removing synthesis gas from the reactor, means for subjecting the synthesis gas to a conversion process comprising an exothermic reaction to produce dimethyl ether in a converter, the converter operating at an operating pressure, said oxygen being provided by air separation at an oxygen pressure, the improvement consisting in that there is no synthesis gas compressor for compressing the synthesis gas which is produced by the reactor which is to be sent to the converter.

The apparatus may comprise a recycle synthesis gas compressor for compressing recycle synthesis gas sent from the converter to upstream the converter.

The apparatus may comprise a carbon dioxide compressor for compressing recycle carbon dioxide gas sent from the converter to upstream the reactor.

A steam turbine may be being coupled to at least one of the synthesis gas compressor, the carbon dioxide compressor, at least one air compressor for compressing air to be separated to form oxygen and an at least one air booster.

BRIEF DESCRIPTION OF THE DRAWING

FIG. 1 is a schematic drawing of an installation according to the invention.

DETAILED DESCRIPTION OF THE INVENTION

The invention will now be described in greater detail with reference to the Figure.

Air 1 is separated in an ASU 3 which produces at least liquid oxygen. Any of the plants using a liquid oxygen vaporisation step by heat exchange with feed air as shown in <<The Technology of Catalytic Oxidations>> by Arpentinier et al., Editions Technip, 2001 or <<Tieftemperaturtechnik>> by Hausen Linde may be used. The air is compressed to 6 bar in compressor 5, purified in adsorbent beds (not shown) and then sent in part to a column of the ASU. Another part of the compressed air is pressurized in a booster 7 to a pressure of 70 bar. The air is expanded, then partially liquefied and is sent either entirely to the medium pressure column as shown or at least in part to the low pressure column. The usual reflux streams are not shown for the sake of simplicity. The heat exchanger serves to warm gaseous streams (not shown) from the columns as well as at least one liquid stream 9. The liquid oxygen 9 is pumped to a pressure of 61 bar and vaporised by heat exchange with the feed air. The gaseous oxygen produced at 60 bar (following pressure drop in the exchanger and pipes) is sent to a reactor 11, which may be a partial oxidation reactor or an autothermal reactor having an entry pressure of 60 bar. The reactor 11 is also fed by natural gas 10 at 60 bar.

Where the operating pressure of the reactor is P, the oxygen is produced and sent to the reactor at a pressure of P+$\Delta$P, P being preferably at least 49 bar and $\Delta$P being greater than zero. The oxygen may be produced at between 50 and 80 bar, preferably above 60 bar or even 70 bar and sent to the reactor at that pressure for the case where the operating pressure of the reactor is 49 bar. The oxygen may either be pumped directly to a pressure between 50 and 80 bar and then vaporised at that pressure in the main heat exchange line or may be pumped to an intermediate pressure, vaporised at the intermediate pressure in the main heat exchange line and then compressed to a pressure between 50 and 80 bar in an oxygen compressor.

Synthesis gas is produced at a pressure of 60 bar and is sent at that pressure to the converter 15 via conduit 13. There is no compressor to compress the synthesis gas since the converter 15 operates with an entry pressure of 50 bar and there is an around 1 to 10 bar pressure drop between the entry of the reactor 11 and the entry of the converter 15 due to the presence of a boiler for raising steam and other devices (not shown).

The converter produces DME as a final product 19. In the case where DME is the final product or one of the final products, the converter may operate according to the single step process or the two steps process described above.

In some processes, methanol is removed from the DME produced by the converter and is recycled to the input of the converter (for example in the Lurgi DME process and the NKK slurry phase process). Unreacted synthesis gas 21 may be recycled from an outlet of the converter 15 to the inlet of the converter 15 following compression in compressor 23. It is also common to recycle carbon dioxide 27 from an outlet of the converter 15 to the inlet of the reactor 11 following compression in compressor 29. Preferably the compressor 5, the booster 7, the carbon dioxide recycle compressor 29 and the recycle synthesis gas compressor 23 are all driven by a single steam turbine 25, the steam being derived from the exothermic process. Failing this at least some of the above mentioned compressors are driven by a steam turbine. EP-A-1102953 describes a steam turbine which is used to drive a main air compressor and an air booster. It is of course possible for separate steam turbines to drive the recycle synthesis gas compressor, the carbon dioxide recycle compressor and one or both of the air compressors. The booster 7 is not an essential element of the air separation unit 3; it is for example possible for air compressor 5 to compress all the air to the vaporization pressure required to gasify the oxygen as described in EP-A-0504029. Since the conversion process is highly exothernic, this process or the synthesis gas may be used to raise steam for the steam turbine 25.

We claim:

1. In a process for the use of a hydrocarbon feedstock by reacting the feedstock in a reactor with oxygen to form a synthesis gas containing at least carbon monoxide, carbon dioxide and hydrogen and subjecting the synthesis gas to a conversion process comprising an exothermic reaction producing dimethyl ether in a converter, the converter operating at an operating pressure, said oxygen being provided to the reactor at an oxygen pressure following separation of cooled compressed air compressed in at least one air compressor, the improvement consisting in that the synthesis gas is produced at a pressure such that the synthesis gas is sent from the reactor to the converter without undergoing a compression step, and the air separation unit supplies oxygen to the reactor at an oxygen pressure greater than the operating pressure of the reactor.

2. The process of claim 1 wherein the synthesis gas is produced at a pressure at least 1 bar higher than the operating pressure of the converter.

3. The process according to claim 1 wherein the hydrocarbon feedstock is natural gas.

4. The process according to claim 1 wherein dimethyl ether and at least one of methanol, carbon dioxide and unreacted synthesis gas are present at the outlet of the converter.

5. The process according to claim 4 wherein the exothermic reaction produces dimethyl ether by a direct process.

6. The process according to claim 4 wherein the exothermic reaction produces dimethyl ether by an indirect process, by converting synthesis gas to methanol and then converting the methanol to dimethyl ether.

7. The process according to claim 4 wherein the converter produces a mixture of methanol and dimethyl ether, the mixture is separated to produce substantially pure dimethyl ether and substantially pure methanol and the substantially pure methanol is recycled to an inlet of the converter.

8. The process according to claim 4 wherein carbon dioxide is present at the outlet of the converter and carbon dioxide produced by the converter is recycled to an inlet of the reactor following compression in a carbon dioxide compressor.

9. The process according to claim 8 wherein at least one of the carbon dioxide compressor and an air compressor and an air booster is coupled to a steam turbine.

10. The process according to claim 4 wherein unreacted synthesis gas is present at the outlet of the converter and unreacted synthesis gas produced by the converter is recycled to an inlet of the converter following compression in a recycle synthesis gas compressor.

11. The process according to claim 10 wherein at least one of the recycle synthesis gas compressor and an air compressor and an air booster is coupled to a steam turbine.

12. The process according to claim 1 wherein the hydrocarbon feedstock reacts with the oxygen in a partial oxidation reactor.

13. The process according to claim 1 wherein the hydrocarbon feedstock reacts with the oxygen in an autothermal reactor.

14. In an apparatus for the use of a hydrocarbon feedstock by reacting the feedstock in a reactor with oxygen to form a synthesis gas containing at least carbon monoxide, carbon dioxide and hydrogen: a reactor, a feedstock conduit for sending the feedstock to the reactor, an oxygen conduit for sending the oxygen to the reactor, a synthesis gas removal conduit for removing synthesis gas from the reactor, said synthesis gas removal conduit being connected to a converter for subjecting the synthesis gas to a conversion process to produce dimethyl ether comprising an exothermic reaction in a converter, the converter operating at an operating pressure, said oxygen being provided by air separation at an oxygen pressure; the improvement consisting in that there is no synthesis gas compressor for compressing the synthesis gas which is produced by the reactor and which is to be sent to the converter.

15. The apparatus according to claim 14 comprising a steam turbine and at least one of at least one air compressor for compressing air to be separated to form oxygen, at least one air booster for further compressing air to be separated to form oxygen, a carbon dioxide compressor for compressing carbon dioxide sent from the converter to the reactor and a recycle synthesis gas compressor for compressing unreacted synthesis gas sent from the converter to upstream the converter, said steam turbine being coupled to at least one of the recycle synthesis gas compressor, the carbon dioxide compressor and an at least one air compressor and an air booster.

* * * * *